US009074262B2

(12) United States Patent
Goudsmit et al.

(10) Patent No.: US 9,074,262 B2
(45) Date of Patent: *Jul. 7, 2015

(54) NUCLEIC ACID SEQUENCES THAT CAN BE USED AS PRIMERS AND PROBES IN THE AMPLIFICATION AND DETECTION OF ALL SUBTYPES OF HIV-1

(71) Applicant: bioMerieux S.A., Marcy-l'Etoile (FR)

(72) Inventors: Jaap Goudsmit, Amsterdam (NL); Pieter Oudshoorn, St. Michielsgestel (NL); Suzanne Jurriaans, Monnickendam (NL); Vladimir Vladimirovich Lukashov, Amsterdam (NL)

(73) Assignee: bioMerieux, B. V., Boxtel (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/226,965

(22) Filed: Mar. 27, 2014

(65) Prior Publication Data
US 2014/0199687 A1 Jul. 17, 2014

Related U.S. Application Data

(60) Division of application No. 11/108,233, filed on Apr. 18, 2005, now Pat. No. 8,697,352, which is a continuation of application No. 09/463,352, filed as application No. PCT/EP98/04945 on Aug. 5, 1998, now Pat. No. 6,881,537.

(30) Foreign Application Priority Data

Aug. 8, 1997 (EP) ...................................... 97202455

(51) Int. Cl.
*C12Q 1/00* (2006.01)
*C07H 21/04* (2006.01)
*C12Q 1/70* (2006.01)

(52) U.S. Cl.
CPC ............... *C12Q 1/703* (2013.01); *Y10S 435/81* (2013.01)

(58) Field of Classification Search
None
See application file for complete search history.

(56) References Cited

U.S. PATENT DOCUMENTS

| 4,772,547 | A | * | 9/1988 | Heimer et al. ..................... 435/5 |
| 4,963,532 | A | * | 10/1990 | Carter .......................... 514/44 R |
| 5,122,457 | A |   | 6/1992 | Reim et al. |
| 5,221,610 | A | * | 6/1993 | Montagnier et al. ............ 435/7.1 |
| 5,306,631 | A |   | 4/1994 | Harrison et al. |
| 5,333,675 | A |   | 8/1994 | Mullis et al. |
| 5,403,707 | A |   | 4/1995 | Atwood et al. |
| 5,413,906 | A |   | 5/1995 | Eberle et al. |
| 5,472,840 | A |   | 12/1995 | Stefano |
| 5,474,796 | A |   | 12/1995 | Brennan |
| 5,576,176 | A |   | 11/1996 | Adams et al. |
| 5,622,820 | A | * | 4/1997 | Rossi ................................ 435/5 |
| 5,622,827 | A | * | 4/1997 | McAllister et al. .......... 435/6.12 |
| 5,629,413 | A |   | 5/1997 | Peterson et al. |
| 5,712,385 | A |   | 1/1998 | McDonough et al. |
| 5,770,428 | A |   | 6/1998 | Boris-Lawrie |
| 6,001,558 | A |   | 12/1999 | Backus et al. |
| 6,025,124 | A |   | 2/2000 | Adams et al. |
| 6,881,537 | B1 |  | 4/2005 | Goudsmit et al. |

FOREIGN PATENT DOCUMENTS

| EP | 0 331 939 A  | 9/1989 |
| EP | 0 331 939 A3 | 9/1989 |
| EP | 0 402 997 A  | 12/1990 |
| EP | 0 402 997 A3 | 12/1990 |
| EP | 0617132 A2   | 8/1993 |
| EP | 0 617 132    | 9/1994 |
| EP | 0 617 132 A  | 9/1994 |
| EP | 0 617 132 A3 | 9/1994 |
| EP | 0 727 497 A1 | 8/1996 |
| EP | 0 887 427 A2 | 12/1998 |
| WO | WO 91/08308  | 6/1991 |

(Continued)

OTHER PUBLICATIONS

Sommer and Tautz, "Minimal homology requirements for PCR primers," Nucleic Acids Research, vol. 17, No. 16, 1989, p. 6749.*
Sommer and Tautz, "Minimal homology requirements for PCR primers," Nucleic Acids Research, vol. 17, No. 16, 1989, p. 6749.*
Muesing et al. "Nucleic Acid Structure and Expression of the Human AIDS/Lymphadenopathy Retrovirus", Nature 313:450-458 (1985).
STN Registry No. 181793-79-3.

(Continued)

*Primary Examiner* — Bradley L Sisson
(74) *Attorney, Agent, or Firm* — Myers Bigel Sibley & Sajovec, P.A.

(57) ABSTRACT

The present invention is related to nucleic acid sequences that can be used in the field of virus diagnostics, more specifically the diagnosis of infections with the AIDS causing Human Immuno-deficiency Virus (HIV). With the present invention nucleotide sequences are provided that can be used as primers and probes in the amplification and detection of HIV-1 nucleic acid. The oligonucleotide sequences provided with the present invention are located in the LTR part of the HIV viral genome. It has been found that, by using the sequences of the present invention in methods for the amplification and detection of nucleic acid a sensitive and specific detection of HIV-1 can be obtained. The benefit of the sequences of the present invention primarily resides in the fact that, with the aid of primers and probes comprising the sequences according to the invention the nucleic acid of all presently known subtypes of HIV-1 can be detected with high accuracy and sensitivity. So far no primer pairs or hybridization probes have been developed that would allow the detection of such a broad range of HIV-1 variants. The oligonucleotide sequences according to the present invention are especially useful in methods for the amplification of nucleic acid.

15 Claims, 1 Drawing Sheet

(56) References Cited

FOREIGN PATENT DOCUMENTS

| WO | WO 91/10746 | 7/1991 |
|---|---|---|
| WO | WO 91 10746 A | 7/1991 |
| WO | WO 93/07259 | 4/1993 |

OTHER PUBLICATIONS

Teglejaerg et al., "Sensitive non-radioactive detection of HIF-1: use of nested primers for the amplification of HIV DNA" Molecular and Cellular Probes (1992) 6: p. 175-180.
"Quantification of HIV-1 Using Multiple Competitors in a Single-Tube Assay" BioTechniques, vol. 21, No. 2 (1996) p. 248-255.
Zazzi et al., "Nested Polymerase Chain Reaction for Detection of Human Immunodeficiency Virus Type 1 DNA in Clinical Specimens" Journal of Medical Virology 32: (1992) p. 172-174.
Engelbrecht et al., "Detection of Southern African human immunodeficiency virus type 1 subtypes by polymerase chain reaction: evaluation of different primer pairs and conditions" Journal of Virological Methods, 55 (1995) p. 391-400.
Innocenti et al., "HIV-1 in Blood Monocytes: Frequency of Detection of Proviral DNA using PCR and Comparison with the Total CD4 Count" AIDS Research and Human Retroviruses, vol. 8, no. 2, (1992) p. 261-268.
Otimann et al., "The Polymerase chain reaction for the detection of HIV-1 genome RNA in plasma from infected individuals" Journal of Virological Methods, 31 (1991) p. 273-284.
Quiros et al., "Human immunodeficiency virus type-1 can be detected in monocytes by polymdase chain reaction" J. Med. Microbiol., vol. 42, (1995) p. 411-414.
McCutchan et al., "Genetic Comparison of Human immunodeficiency Virus (HIV-1) Isolates by Polyemiase Chain Reaction" Journal of Acquired Immune Deficiency Syndrome 4, (1991) p. 1241-1250.
Bell and Ratner "Specificity of Polymerase Chain Amplification Reactions for Human Immunodeficiency Virus Type 1 Dna Sequences" *AIDS Research and Human Retroviruses* 5(1):87-95 (1989).
Böni et al. "PCR Identification of HIV-1 DNA Sequences in Brain Tissue of Patients with AIDS Encephalopathy" *Neurology* 43:1813-1817 (1993).
Goto et al. "Detection of Proviral Sequences in Saliva of Patients Infected with Human Immunodeficiency Virus Type 1" *AIDS Research and Human Retroviruses* 7(3):343-347 (1991).
Karikó "Identification of Conserved Sequences for PCR Primer Design by Multiple Alignments of Dot Matrix Plots" *BioTechniques* 18(6):1048-1049 (1995).
Map of 5' LTR from HIV-1 reference genome (GenBank Accession No. K03455).
Oehlenschlager et al. "Detection of HIV-1 RNA by Nucleic Acid Sequence-Based Amplification Combined with Fluorescence Correlation Spectroscopy" *Proc. Natl. Acad. Sci. USA* 93:12811-12816 (1996).
Scientific Report on Computer Analysis of the Alignment of the HIV LTR Sequence from the Dec. 1996 Edition of the Human Retroviruses and AIDS Compendium published by the Los Alamos National Laboratory, New Mexico.
Revets et al. "Comparative Evaluation of NASBA HIV-1 RNA QT, AMPLICOR-HIV Monitor, and QUANTIPLEX HIV RNA, Three Methods for Quantification of Human Immunodeficiency Virus Type 1 RNA in Plasma" *Journal of Clinical Microbiology* 34(5):1058-1064 (1996).
LTR alignment from the Dec. 1996 Edition of the Human Retroviruses and AIDS Compendium published by the Los Alamos National Laboratory, New Mexico.
Partial gag alignment from the Dec. 1996 Edition of the Human Retroviruses and AIDS Compendium published by the Los Alamos National Laboratory, New Mexico.
Van Gemen et al. "Quantification of HIV-1 RNA in Plasma Using NASBA™ During HIV-1 Primary Infection" *Journal of Virological Methods* 43:177-188 (1993).
File history of European patent application serial No. EP 98943872.6, filed Aug. 5, 1998.
De Baar et al., *Journal of Clinical Microbiology*, vol. 37, No. 6, Jun. 1999, pp. 1813-1818.
Research Genetics, "Designer PCR," *Nucleic Acids Research*, vol. 22, No. 15, Aug. 1994.
Sommer and Tautz, "Minimal homology requirements for PCR primers," *Nucleic Acids Research*, vol. 17, No. 16, p. 6749, 1989.
Zaaijer et al., *Journal of Virological Methods*, vol. 52, 1995, pp. 175-181.
Christopherson et al. "The effects of internal primer-template mismatches on RT-PCR: HIV-1 model studies" *Nucleic Acids Research* 25(3):654-658 (1997).
Engelbrecht et al. "Detection of Southern African human immunodeficiency virus type 1 subtypes by polymerase chain reaction: evaluation of different primer pairs and conditions" *Journal of Virological Methods* 55:391-400 (1995).
Yang et al. "Flow Cytometric Immunodetection of Human Immunodeficiency Virus Type 1 Proviral DNA by Heminested PCR and Digoxigenin-Labeled Probes" *Clinical and Diagnostic Laboratory Immunology* 1:26-31 (1994).
Dahlen et al. "Detection of Human Immunodeficiency Virus Type 1 by Using the Polymerase Chain Reaction and a Time-Resolved Fluorescence-Based Hybridization Assay" *Journal of Clinical Microbiology* 29(4):798-804 (1991).
Kievits et al. "NASBA™ isothermal enzymatic in vitro nucleic acid amplification optimized for the diagnosis of HIV-1 infection" *Journal of Virological Methods* 35:273-286 (1991).
Coutlée et al. "The polymerase chain reaction: a new tool for the understanding and diagnosis of HIV-1 infection at the molecular level" *Molecular and Cellular Probes* 5:241-259 (1991).
File history of European patent application serial No. EP98943872.5, filed Aug. 5, 1998, record current through Feb. 1, 2006 (summary and each document listed from May 5, 2004 through Feb. 1, 2006; earlier documents submitted in parent U.S. Appl. No. 09/463,352 and in earlier filed Information Disclosure Statment).
File history of European Patent No. 1002138 (Application No. EP 98943872.6) from Mar. 21, 2006 through Aug. 16, 2007.
STN Accession No. RN 159610-32-9, accessed Feb. 17, 2009.
STN Accession No. RN 96098-40-7, accessed Feb. 17, 2009.
File history of European patent application serial No. EP 98943872.6-2404 / 1002138, filed Aug. 5, 1998, record current through Jul. 17, 2008 (summary of each document listed from Aug. 16, 2007 through Jul. 17, 2008; earlier document submitted in parent U.S. Appl. No. 09/463,352 and in earlier filed Information Document Statement).

\* cited by examiner

NUCLEIC ACID SEQUENCES THAT CAN BE USED AS PRIMERS AND PROBES IN THE AMPLIFICATION AND DETECTION OF ALL SUBTYPES OF HIV-1

RELATED APPLICATIONS

This application is a divisional of U.S. application Ser. No. 11/108,233, filed Apr. 18, 2005, which is a continuation of U.S. application Ser. No. 09/463,352, filed Jan. 21, 2000, now U.S. Pat. No. 6,881,537, which is a 35 U.S.C. §371 national phase application of International Application No. PCT/EP98/04945; filed on Aug. 5, 1998, which claims priority to European Patent Application No. 97202455.8, filed Aug. 8, 1997. The entire contents of each of these applications is fully incorporated herein by reference.

The present invention is related to nucleic acid sequences that can be used in the field of virus diagnostics, more specifically the diagnosis of infections with the AIDS causing Human immunodeficiency Virus (HIV).

Whereas conventional virus diagnosis has been based predominantly on the detection of viral antigens or specific antibodies thereto, in recant years attention has shifted towards methods for the direct detection of the genome of viruses or nucleic acid sequences derived thereof, both RNA and DNA. These methods are usually based on nucleic acid hybridization. Nucleic acid hybridization is based on the ability of two strands of nucleic acid containing complementary sequences to anneal to each other under the appropriate conditions, thus forming a double stranded structure. When the complementary strand is labeled, the label can be detected and is indicative for the presence of the target sequence. Especially in combination with methods for the amplification of nucleic acid sequences these methods have become an important tool in viral diagnosis, in particular for the detection of human immunodeficiency virus (HIV).

Nucleic acid amplification techniques are especially useful as an additional technique in cases where serological methods give doubtful results or in cases where there may be a considerable time period between infection and the development of antibodies to the virus. With HIV, seroconversion usually can occur some 3-6 months after exposure to the virus. Thus, whereas no antibodies will be detected with conventional immunoassays, proviral DNA or circulating viral RNA may already be detectable. Also in monitoring antiviral therapy, methods based on nucleic acid amplification have several advantages over serological methods. Especially quantitative amplification methods provide a powerful tool in assessing the changes in the amount of virus present before and during therapy.

The choice of the oligonucleotides to be used as primers and probes in the amplification and detection of nucleic acid sequences is critical for the sensitivity and specificity of the assay. The sequence to be amplified is usually only present in a sample (for example a blood sample obtained from a patient suspected of having a viral infection) in minute amounts. The primers should be sufficiently complementary to the target sequence to allow efficient amplification of the viral nucleic acid present in the sample. If the primers do not anneal property (due to mispairing of the bases on the nucleotides in both strands) to the target sequence, amplification is seriously hampered. This will effect the sensitivity of the assay and may result in false negative test results. Due to the heterogeneity of viral genomes false negative test results may be obtained if the primers and probes are capable of recognizing sequences present in only part of the variants of the virus. The HIV virus shows a high heterogeneity. Genetic variability has been demonstrated amongst isolates from different continents but also between individuals and between different stages of the disease. Based on sequence analysis two groups within HIV-1 have been identified: group M (M for "major"), and group O (O for "outlier"). Within group M subtypes (A-H), each constituting a phylogenetic separate set of sequences, have been assigned and additional ones are being Identified. This sequence variation is not uniformly distributed throughout the genome. The HIV-1 genome, like all retroviral genomes, roughly consists of the following regions. The gag gene of the HIV-1 genome is the region encoding the core proteins of the virus (for example, p24). The env gene encodes a large precursor protein, gp160, which is processed into the envelop proteins gp120 and gp41. The pot gene encodes the polymerase of the virus (reverse transcriptase). The Long Terminal Repeat region's (LTR's) are the regions on the viral genome that participate in the integration of the virus with the host cell and in the regulation of transcription of the viral genes. Some regions are more prone to sequence variation than others. Especially in the any domain sequence variation can be as high as 30% between members of the different subtypes. Ideally, primer selection should be based on knowledge of interstrain variability in candidate primer sequences and the consequences of mismatching at primer sites. McCutchan et al, J. AIDS, 4, 1241-1250, 1991, used PCR to make a genetic comparison of different HIV-1 isolates. Using anchored PCR (varying sense primers were used with a constant antisense primer. primers were chosen from relatively conserved regions in gag, any and LTR) The effect of primer mispairing on the amount of PCR product obtained was also investigated. Mispairing at the 3' end of the primer decreased the amount of product sometimes more then 100-fold.

The detection of all presently known subtypes of HIV-1 is of extreme importance, especially with regard to patient management, security of blood and blood products and clinical- and epidemiological studies. Current assays for the amplification and subsequent detection of HIV-1 derived nucleic acid sequences are usually based on amplification of sequences in the gag region of the viral genome. These assays have been developed for subtype B, which is the major subtype in European countries and the United States. However, the presence of other subtypes, which were geographically confined before, is increasing due to frequent travel between these countries and, for example, African countries. Sensitive assays are therefore needed that are capable of detecting as much variants of the HIV-1 virus as possible (preferably all).

Research aimed at identifying suitable primer sets for the reliable amplification of HIV-1 derived nucleic acid sequences has been ongoing for the past years. Engelbrecht et al., J. Virol. Meth., 55, 391-400, 1995, describe a study aimed at the development of a specific and sensitive PCR protocol using env, gag and LTR primer pairs to detect subtypes present in the Western Cape, South Africa. Twenty four strains of which it was known that they belonged to subtypes B, C and D were analyzed. It was found that the performance of the primer pairs was greatly dependent on the optimization of the reaction conditions for the different primer pairs. Only when less stringent conditions were used (for example, with the LTR primer pair an increased cycle time and lower annealing temperatures were required) these particular strains of HIV could be detected with sufficient sensitivity and reproducibility with all primer pairs.

Zazzi et al., J. Med. Virol., 38, 172-174, 1992, developed a two-step PCR reaction (using nested primers) for the detection of HIV-1 DNA in clinical samples. The primers used for amplification were derived from the gag gene and the LTR region. The patients tested in this study were all from neighbouring areas., which makes it likely that they represent only a limited number of different viral strains.

A quantitative PCR method using LTR derived nested primers was described by Vener et al. in BioTechniques, 21, 248-255, 1996. This procedure was only tested on HIV-1$_{MN}$ Infected peripheral blood mononuclear cells (PBMC). Thus nothing can be said about the suitability of the primers used for detecting different subtypes of the virus.

With the present invention nucleotide sequences are provided that can be used as primers and probes in the amplification and detection of HIV-1 nucleic acid. The oligonucleotide sequences provided with the present invention are located in the LTR part of the HIV viral genome. It has been found that, by using the sequences of the present invention in methods for the amplification and detection of nucleic acid a sensitive and specific detection of HIV-1 can be obtained. The benefit of the sequences of the present invention primarily resides in the fact that, with the aid of primers and probes comprising the sequences according to the invention the nucleic acid of all presently known subtypes of HIV-1 can be detected with high accuracy and sensitivity. So far no primer pairs or hybridization probes have been developed that would allow the detection of such a broad range of HIV-1 variants.

The oligonucleotide sequences according to the present invention are especially useful in methods for the amplification of nucleic acid.

Various techniques for amplifying nucleic acid are known in the art. One example of a technique for the amplification of a DNA target segment is the so-called "polymerase chain reaction" (PCR). With the PCR technique the copy number of a particular target segment is increased exponentially with a number of cycles. A pair of primers is used and in each cycle a DNA primer is annealed to the 3' side of each of the two strands of the double stranded DNA-target sequence. The primers are extended with a DNA polymerase in the presence of the various mononucleotides to generate double stranded DNA again. The strands of the double stranded DNA are separated from each other by thermal denaturation and each strand serves as a template for primer annealing and subsequent elongation in a following cycle. The PCR method has been described in Saiki et al., Science 230, 135, 1985 and in European Patents no. EP 200362 and EP 201184.

Another technique for the amplification of nucleic acid is the so-called transcription based amplification system (TAS). The TAS method is described in International Patent Appl. no. WO 88/10315. Transcription based amplification techniques usually comprise treating target nucleic acid with two oligonucleotides one of which comprises a promoter sequence, to generate a template including a functional promoter. Multiple copies of RNA are transcribed from said template and can serve as a basis for further amplification.

An Isothermal continuous transcription based amplification method is the so-called NASBA process ("NASBA") as described in European Patent no. EP 329822. NASBA includes the use of T7 RNA polymerase to transcribe multiple copies of RNA from a template including a T7 promoter. Other transcription based amplification techniques are described in EP 408295. EP 408295 is primarily concerned with a two-enzyme transcription based amplification method. Transcription based amplification methods, such as the NASBA method as described in EP 329822, are usually employed with a set of oligonucleotides, one of which is provided with a promoter sequence that is recognized by a DNA dependent RNA polymerase such as, for example, T7 polymerase. Several modifications of transcription based techniques are known in the art. These modifications comprise, for example, the use of blocked oligonucleotides (that may be provided with a promoter sequence). These olgo's are blocked so as to Inhibit an extension reaction proceeding therefrom (U.S. Pat. No. 5,554,516). One or more "promoter-primers" (oligonucleotides provided with a promoter sequence) may be used in transcription based amplification techniques, optionally combined with the use of one or more oligonucleotides that are not provided with a promoter sequence. For RNA amplification, a transcription based amplification technique, is a preferred technology. Amplification Using PCR, can also be based on an RNA template. The actual PCR needs to be preceded by a reverse transcription step to copy the RNA into DNA (RT-PCR). However, if RT-PCR is used for the detection of viral transcripts differentiation of mRNA- and DNA-derived PCR products is necessary. DNAse treatment prior to RT-PCR can be employed (Bitsch, A. et al., J. Infect. Dis 167, 740-743, 1993; Meyer, T. et al., Mol. Cell. Probes. 8, 261-271, 1994), but sometimes fails to remove contaminating DNA sufficiently (Bitsch, A. et al., 1993).

In contrast to RT-PCR. NASBA, which is based on RNA transcription by T7 RNA polymerase (Kievits et al., 1991; Compton, 1991), does not need differentiation between RNA- and DNA-derived amplification products since it uses RNA as its principal target NASBA enables specific amplification of RNA targets even in a background of DNA.

The use of the oligonucleotides according to the invention is not limited to any particular amplification technique or any particular modification thereof. It is evident that the oligonucleotides according to the invention find their use in many different nucleic acid amplification techniques and various methods for detecting the presence of (amplified) nucleic acid of HIV. The oligonucleotides of the present invention can likewise be used in quantitative amplification methods. An example if such quantitative method is described in EP 525882.

The term "oligonucleotide" as used herein refers to a molecule comprised of two or more deoxyribonucleotides or ribonucleotides. Such oligonucleotides may be used as primers and probes.

Of course, based on the sequences of the oligonucleotides of the present invention, analogues of oligonucleotides can also be prepared. Such analogues may constitute alternative structures such as "PNA" (molecules with a peptide-like backbone Instead of the phosphate sugar backbone of normal nucleic acid) or the like. It is evident that these alternative structures, representing the sequences of the present invention are likewise part of the present invention.

The term "primer" as used herein refers to an oligonucleotide either naturally occurring (e.g. as a restriction fragment) or produced synthetically, which is capable of acting as a point of initiation of synthesis of a primer extension product which is complementary to a nucleic acid strand (template or target sequence) when placed under suitable conditions (e.g. buffer, salt, temperature and pH) in the presence of nucleotides and an agent for nucleic acid polymerization, such as DNA dependent or RNA dependent polymerase. A primer must be sufficiently long to prime the synthesis of extension products in the presence of an agent for polymerization. A typical primer contains at least about 10 nucleotides in length of a sequence substantially complementary or homologous to the target sequence, but somewhat longer primers are preferred. Usually primers contain about 15-26 nucleotides but longer primers may also be employed, especially when the primers contain additional sequences such as a promoter sequence for a particular polymerase.

Normally a set of primers will consist of at least two primers, one 'upstream' and one 'downstream' primer which together define the amplificate (the sequence that will be amplified using said primers).

Primarily for the use in transcription based amplification techniques, the oligonucleotides according to the invention may also be linked to a promoter sequence. The term "promoter sequence" defines a region of a nucleic acid sequence that is specifically recognized by an RNA polymerase that binds to a recognized sequence and initiates the process of transcription by which an RNA transcript is produced. In principle any promoter sequence may be employed for which there is a known and available polymerase that is capable of recognizing the initiation sequence. Known and useful promoters are those that are recognized by certain bacteriophage RNA polymerases such as bacteriophage T3, T7 or SP6. Olgonucleotides linked to a promoter sequence are commonly referred to as "promoter primers". Their function as a primer, e.g. the starting point for an elongation reaction, however, may be blocked, as already mentioned above, or absent in some embodiments of transcription based amplification reactions.

An oligonucleotide according to the present invention is substantially complementary to a sequence of the LTR region of a nucleic acid sequence of a HIV genome, said oligonucleotide being 10-50 nucleotides in length and comprising, at least a fragment of 10 nucleotides, of a sequence selected from the group consisting of:

```
SEQ ID 1:
G GGC GCC ACT GCT AGA GA

SEQ ID 2:
G TTC GGG CGC CAC TGC TAG A

SEQ ID 3:
CGGGCGCCACTGCTA

SEQ ID 4:
CTG CTT AAA GCC TCA ATA AA

SEQ ID 5:
CTC AAT AAA GCT TGC CTT GA

SEQ ID 6:
TCT GGT AAC TAG AGA TCC CTC

SEQ ID 7:
TAG TGT GTG CCC GTC TGT

SEQ ID 8:
AGT GTG TGC CCG TCT GTT

SEQ ID 12:
GAT GCA TGC TCA ATA AAG CTT GCC TTG AGT
``` or the complementary sequence thereof.

It is understood that oligonucleotides consisting of the sequences of the present Invention may contain minor deletions, additions and/or substitutions of nucleic acid bases, to the extent that such alterations do not negatively affect the yield or product obtained to a significant degree. Where oligonucleotides according to the present invention are used as probes, the alterations should not result in lowering the hybridization efficiency of the probe. For example, in case of transcription based amplification techniques, wherein one or more of the primers may be provided with a promoter sequence, the introduction of a purine-rich (=G or A) hybridizing sequence, Just after the promoter sequence may have positive effects on the transcription (when there are C's and T's abortive transcription may occur). If no such sequence is available in the target nucleic acid a purine-rich sequence can be inserted in the oligonucleotide Just following the last three G residues of the promoter sequence.

The sequences of the present invention are reflected as DNA sequences. The RNA equivalents of these sequences are likewise part of the present invention.

Preferred oligonucleotides according to the invention are oligonucleotides consisting essentially of a sequence selected from the group consisting of:

```
SEQ ID 1:
G GGC GCC ACT GCT AGA GA

SEQ ID 2:
G TTC GGG CGC CAC TGC TAG A

SEQ ID 3:
CGGGCGCCACTGCTA

SEQ ID 4:
CTG CTT AAA GCC TCA ATA AA

SEQ ID 5:
CTC AAT AAA GCT TGC CTT GA

SEQ ID 6:
TCT GGT AAC TAG AGA TCC CTC

SEQ ID 7:
TAG TGT GTG CCC GTC TGT.

SEQ ID 8:
AGT GTG TGC CCG TCT GTT.

SEQ ID 9:
aat tct aat acg act cac tat agg gAG AGG GGC GCC ACT GCT AGA GA
```

-continued

SEQ ID 10:
aat tct aat acg act cac tat agg gAG AGg TTC GGG CGC CAC TGC TAG A

SEQ ID 11:
aat tct aat acg act cac tat agg gCGGGCGCCACTGCTA

SEQ ID 12:
GAT GCA TGC TCA ATA AAG CTT GCC TTG AGT

SEQ ID 9-11 actually comprise the sequence as reflected by SEQ ID 1-3. In SEQ ID 9-11, the sequences of SEQ ID 1-3 are operably linked to a promoter sequence (the T7 promoter sequence). This makes the sequences especially suitable for use as upstream primer in a transcription based amplification technique such as NASBA.

A preferred embodiment of the present invention is a combination of two oligonucleotides according to the invention, for use as a set in nucleic acid amplification.

Such a pair of oligonucleotides, for use as a set in the amplification of a target sequence located within the LTR region of the genome of HIV-1, consists of a first oligonucleotide being 10-50 nucleotides in length and comprising, at least a fragment of 10 nucleotides, of a sequence selected from the group consisting of:

SEQ ID 1:
G GGC GCC ACT GCT AGA GA

SEQ ID 2:
G TTC GGG CGC CAC TGC TAG A

SEQ ID 3:
CGGGCGCCACTGCTA and a second oligonucleotide being 10-50 nucleotides in length and comprising, at least a fragment of 10 nucleotides, of a sequence selected from the group consisting of:

SEQ ID 4:
CTG CTT AAA GCC TCA ATA AA

SEQ ID 5:
CTC AAT AAA GCT TGC CTT GA.

SEQ ID 12:
GAT GCA TGC TCA ATA AAG CTT GCC TTG AGT

One of the oligonucleotides may serve as an "upstream oligonucleotide", i.e., an upstream-primer, while the second oligonucleotide serves as a "downstream oligonucleotide", i.e. downstream primer, in the amplification reaction. The location on the HIV-genome (or the sequence complementary thereto) to which both oligonucleotides comprised in such a pair according to the Invention can anneal, will together define the sequence of the nucleic acid that is amplified. The amplified sequence is located between the "primer-binding sites" within the LTR region of the HIV-genome. It has been found that, by using a pair of oligonucleotides according to the invention in an amplification reaction, accurate and reliable amplification of nucleic acid derived from all presently know sub-types of HIV can be achieved.

A most preferred pair of oligonucleotides according to the invention will consist of a first primer comprising the sequence of SEQ ID NO 1 and a second primer with the sequence of SEQ ID NO 5. For use in a transcription based amplification method, the oligonucleotide with SEQ ID NO 9 is preferred, in combination with an oligonucleotide with the sequence of SEQ ID NO 5.

Part of the oligonucleotides according to the invention are particularly suitable for use as a probe in the detection of nucleic acid amplified with a pair of oligonucleotides according to the invention. When used as a probe, said oligonucleotides may be provided with a detectable label. Olgonucleotides according to the invention that are especially suitable as a probe consist essentially of the sequence

SEQ ID 6:
TCT GGT AAC TAG AGA TCC CTC

SEQ ID 7:
TAG TGT GTG CCC GTC TGT
or

SEQ ID 8:
AGT GTG TGC CCG TCT GTT provided with a detectable label. A most preferred oligonucleotide in this respect is an oligonucleotide with a sequence as depicted in SEQ ID 6.

Various labeling moieties are known in the art Said moiety may, for example, either be a radioactive compound, a detectable enzyme (e.g. horse radish peroxidase (HRP)), a hapten like blotin, or any other moiety capable of generating a detectable signal such as a colorimetric, fluorescent, chemiluminescent or electrochemiluminescent signal.

Hybrids between oligonucleotides according to the invention and (amplified) target nucleic acid may also be detected by other methods known to those skilled in the art.

Evidently methods for amplification of nucleic acid, like the ones that have been mentioned above, using the oligonucleotides according to the present invention are also part of the invention.

The present invention further provides test kits for the amplification and detection of HIV nucleic acid. The use of said test-kits enables accurate and sensitive screening of samples suspected of containing HIV derived nucleic acid. Such test-kits may contain a pair of oligonucleotides according to the invention and optionally also a oligonucleotide according to the invention that can be used as a probe for the detection of the amplified material. Furthermore the test-kit may contain suitable amplification reagents. These reagents are for example the suitable enzymes for carrying out the amplification reaction. A kit, adapted for use with NASBA, for example may contain suitable amounts of reverse transcriptase, RNase H and T7 RNA polymerase. Said enzymes may be present in the kit in a buffered solution but can likewise be provided as a lyophilized composition, for example, a lyophilized spherical particle. Such lyophilized particles have been disclosed in PCT appl. no. EP95/01288. The kit may further be furnished with buffer compositions, suitable for carrying out an amplification reaction. Said buffers may be optimized for the particular amplification technique for which the kit is intended as well as for use with the particular oligonucleotides that are provided with the kit. In transcription based amplification techniques, such as NASBA, said buffers may contain, for example, DMSO, which enhances the amplification reaction (as is disclosed in PCT appl. no. US90/04733).

Furthermore the kit may be provided with an Internal control as a check on the amplification procedure and to prevent the occurrence of false negative test results due to failures in the amplification procedure. The use of internal controls in transcription based amplification techniques is described in PCT appl. no. EP 93/102248. An optimal control sequence is selected in such a way that it will not compete with the target nucleic acid in the amplification reaction. Kits may also contain reagents for the isolation of nucleic acid from biological specimen prior to amplification. A suitable method for the Isolation of nucleic acid is disclosed in EP389063.

Figure 1A:
FIG. 1.

Amplification products after blotting and detection by enhanced chemiluminescence obtained after amplification in presence (panel A) or absence (panel B) of HIV-1 RNA using the following primer pairs. Lane 1: SEQ ID 9-SEQ ID 10, lane 2: SEQ ID 9-SEQ ID 5, lane 3: SEQ ID 10-SEQ ID 4, lane 4: SEQ ID 10-SEQ ID 5, lane 5: SEQ ID 3-SEQ ID 12.

EXAMPLES

Example 1

Amplification and Detection of HIV-1 Genomic RNA

The following procedures were applied to amplify and detect HIV-1 genomic RNA from samples as described in the following examples.

Sample Preparation and Nucleic Acid Isolation.

The isolation of the nucleic acids was performed according to Boom et al., 1990, Journal of Clinical Microbiology 28, 495-503 and European patent no. EP0389083. In short: A volume of 200 µl of pooled plasma's from healthy donors (negative for HBsAg, anti-HIV and anti-HCV) was added to 9001 of lysis buffer (47 mM Tris-HCl pH 7.2, 20 mM EDTA, 1.2% Triton X-100, 4.7 M guanidine thiocyanate (GuSCN, Fluka, Buchs, Switzerland)). After vortexing and centrifugation (30 seconds, 13,000 rpm) a dilution series of HIV-1 RNA subtype B standard, characterised and described by Layne et al., 1992, Virology 189, 695-714 or HIV-1 positive specimens, was added. Upon addition of 50 µl activated silicon (0.4 g/ml suspension in 0.1 N HCl), the suspension was incubated for 10 minutes at room temperature with regular vortexing. After centrifugation (30-60 seconds, 13,000 rpm) the silicon pellet was washed twice with 1 ml of wash buffer (5.25 M GuSCN, 50 mM Tris-HCl pH 6.4), followed by two 70% ethanol washes and one acetone wash step. Subsequently, the silicon pellets were dried during ten minutes in a 56° C. heating block. The nucleic acids were eluted from the silicon by adding 50 µl elution buffer (1.0 mM Tris-HCl, pH 8.5) and incubation at 56° C. for 10 minutes. Subsequently, 5 µl of the eluate was taken of the pellet for further use in the amplification reaction. The remaining eluate was stored at −70° C.

NASBA Amplification.

Amplifications were carried out in a reaction volume of 20 µl which is composed of 10 µl primer mixture, 5 µl (isolated) nucleic acids and 5 µl enzyme mixture. The primer mixture was made by reconstitution of a lyophilised accusphere into 50 µl accusphere diluent, 51.6 µl water, 8.4 µl 2 M KCl and 5 µl of each primer (10 µM). The mixture was thoroughly vortexed before use. From this primer mixture 10 µl was added to 5 µl of the (Isolated) HIV-1 RNA (standard). This mixture was Incubated for 5 minutes at 65° C. and subsequently incubated at 41° C. for another 5 minutes. After these incubations 5 µl enzyme mixture was added and incubated for 5 minutes at 41° C. The tubes were transferred to the detection area and incubated for 90 minutes at 41° C. After the amplification reaction the tubes were stored at −20° C. until further use.

Each amplification reaction contained the following reagents:

40 mM Tris-HCl, pH 8.5
12 mM $MgCl_2$
70 mM KCl
15% v/v dimethyl sulfoxide
5 mM dithiothreitol
1 mM of each deoxynucleoside triphosphate
2 mM of the nucleosides rATP, rCTP, rUTP
1.5 mM rGTP
0.5 mM ITP
0.105 µg/µl BSA
0.08 units RNaseH
32 units $T_7$ RNA polymerase
6.4 units avian myloablastosis virus reverse transcriptase (Seikagaku, USA)
0.2 µM of each primer
375 mM sorbitol
45.6 mM sucrose
28.5 mM mannitol
0.13 mM dextran T40

Detection of the Amplified Products.

A. Gel Electrophoresis.

The presence of amplified products was analysed using an agarose gel (100 ml of 2% Pronarose and 0.5 µg/ml ethidium bromide) and 1*TAE (40 mM Tris-acetate, 1 mM EDTA pH 8.0) running buffer are used. Electrophoresis was carried out at 100 volts for approximately 30 minutes. The ethidium bromide-stained bands of the amplified products were visualised using UV radiation. The blot was hybridised with biotin probe (3 µM) in hybridisation mix (750 mM NaCl, 75 mM sodumnitrate, 20 mM $NatHPO_4NaH_2PO_4$ (pH 6.7), 10*Denhardts) by Incubating the blot for 4 hours at 50° C. After hybridisation the blot was washed two times for 5 minutes at 50° C. with 450 mM NaCl, 45 mM sodiumcitrate pH 6.4 (2*SSPE) and 1% sodium dodecyl sulphate (SDS) solution and one time for 10 minutes with 20 mM $NaeHPO_4$ pH 7.4, 360 mM NaCl, 2 mM EDTA and 0.1% SDS at room temperature. Subsequently, the blot was incubated for 30 minutes with 2 µl streptavidin/horse radish peroxidase solution (500 U/ml from the enhanced chemiluminiscense detection kit of Amersham Life Science) in 10 ml 50 mM $Na_2HPO_4$. 900 mM NaCl, 5 mM EDTA, pH7.4 and 0.5% SDS. Following washes respectively two times for 5 minutes in 2*SSPE, 0.1% SDS and once for 10 minutes in 2*SSPE at room temperature the blot was dried between tissues, developed and exposed to a film according to the Amersham kit protocol.

B. Electrochemiluminescence (ECL) Probe Hybridisation.

The amplification products were diluted two times in detection diluent (1.0 mM Tris/HCl, pH 8.5 and 0.2 g/l 2-methyllsothiazolone HCl). Subsequently, 5 µl of the diluted amplification product was incubated for 30 minutes at 41° C. with 0.084 µM of the HIV-1 specific blotin probe bound to 5 µg streptavidin-coated magnetic beads (mean size 2.8 µm±0.2 µm, Dynal, Great Neck, N.Y., USA) and $2*10^{11}$ molecules of an ECL (Tris(2,2-bipyridine) ruthenium [II] complex)-labelled probe, in a total volume of 25 µl 750 mM NaCl, 75 mM sodumcirate, pH 6.4 (5*SSC). As negative controls, detection diluent was also incubated with the bead-probe and ECL-probe mixtures. During incubation, tubes were agitated every 10 minutes to keep the beads in suspension. Subsequently, 300 μl of assay buffer solution (100 mM tripropylamine, pH 7.5) was added and the tubes were placed in an ECL detection instrument (NASBA QR-system from Organon Teknika BV) for reading the emitted ECL signals.

Example 2

Amplification and Detection of HIV-1 Genomic RNA

Figure 1B:

The following primer pairs were tested on $10^4$ copies (as determined by spectrophotometry at 260 nm) of the HIV-1 RNA standard. The RNA was added directly into the amplification. The analysis of the amplified products was performed by gel electophoresis as described in example 1. The results are shown in the FIG. 1.

All primer pairs and probes of the present invention were able to amplify and detect HIV-1 RNA from subtype B to a similar extent Analytical sensitivity is shown for two primer pairs (SEQ ID 9/SEQ ID 5 and SEQ ID11/SEQ ID 5) using a dilution series of the HIV-1 RNA standard which has an initial concentration of $5.5*10^9$ copies/ml. The detection was done with probes having the sequences as depicted in SEQ ID 7 and SEQ ID 6. The amplification and detection was carried out as described in example 1. Table 1 shows the results obtained with both primer pairs.

TABLE 1

| HIV-1 RNA | SEQ ID 3-SEQ ID 5 | | SEQ ID 9-SEQ ID 5 | |
|---|---|---|---|---|
| copies | No. detected | % detected | No. detected | % detected |
| 200 | 4:4 | 100% | 4:4 | 100% |
| 100 | 8:8 | 100% | 8:8 | 100% |
| 50 | 8:8 | 100% | 8:8 | 100% |
| 25 | 7:8 | 87.5% | 7:8 | 87.5% |
| 12 | 6:8 | 75% | 4:8 | 50% |
| 6 | 2:8 | 25% | 4:7 | 57% |
| 3 | 0:8 | 0% | 2:7 | 28.5% |
| 0 | 0:8 | 0% | 0:7 | 0% |

Both primer pairs have approximately the same sensitivity for the HIV-1 RNA standard respectively a detection rate of 70% for the primer pair SEQ ID 9/SEQ ID 5 and a detection rate of 63% for the primer pair SEQ ID 3/SEQ ID 5.

Example 3

Amplification and Detection of HIV-1 RNA in Presence of an Internal Control

In this example the primer pair SEQ ID 9/SEQ ID 5 and probe with the sequence of SEQ ID 7 was tested on dilution series of the HIV-1 RNA standard in presence of an Internal control (ic-) RNA. The ic-RNA is an in vitro transcript which contains part of the LTR sequence of HIV-1 HXB-2 and $10^4$ copies (as determined by spectrophotometry at 260 nm) are added prior to nucleic acids isolation. The isolation, amplification and ECL detection was performed as described in example 1. As a comparison, separate amplification and detection was performed using a primer pair located in the HIV-1 gag region (P1/P2) previously described by Van Gemen et al, 1993, Journal of Virological Methods 43, 177-188. The probes used to detect the amplification products generated by the gag based primer pair were:

```
Biotin probe:    5'-TGTTAAAAGAGACCATCAATGAGGA.
ECL probe:       5'-GAATGGGATAGAGTGCATCCAGTG.
```

Results are shown in Table 2.

TABLE 2

| HIV-1 RNA copies/ | LTR SEQ ID 9-SEQ ID 5 | | GAG P1/P2 | |
|---|---|---|---|---|
| 200 μl | No. detected | % detected | No. detected | % detected |
| 320 | 9:10 | 90% | nt* | nt* |
| 160 | 5:10 | 50% | 8:10 | 80% |
| 80 | 5:10 | 50% | 5:10 | 50% |
| 40 | 3:8 | 38% | 4:10 | 40% |
| 20 | 3:10 | 32% | 1:10 | 10% |
| 10 | 1:10 | 10% | 2:10 | 20% |
| 0 | 0:5 | 0% | 1:5 | 20% |

*nt is not tested.

Both the LTR primer pair of this example and the gag primer pair were able to detect a similar amount of HIV-1 RNA in an assay controlled by an in vitro produced RNA which was added prior to the nucleic acids isolation.

Example 4

Detection of HIV-1 RNA in HIV-1 Positive Samples

In this example, 40 HIV-1 positive samples from various geographical locations were analysed for presence of HIV-1 RNA. All samples were isolated by the nucleic acids isolation method described in example 1. Amplification and detection were carried out as described in example 1 using primer pair SEQ ID 9/SEQ ID 5 and probe with the sequence of SEQ ID 7 or probe with the sequence of SEQ ID 8.

For comparison, separate amplification and detection was carried out using the gag primer pair and probes as described in example 3. Presence of amplified products was detected by ECL probe hybridisation according to the method of example 1. Result are shown in Table 3.

TABLE 3

| Primer pair | ECL Probe | No. Detected | % Detected. |
|---|---|---|---|
| SEQ ID 9/SEQ ID 5 (LTR) | SEQ ID 7 | 40/40 | 100% |
| SEQ ID 9/SEQ ID 5 (LTR) | SEQ ID 8 | 10/10 | 100% |
| P1/P2 (gag) | | 29/40 | 72.5% |

Both primer probe combinations derived from the LTR region of HIV-1 described in this example were able to detect HIV-1 from all the samples tested. In contrast, the primer probe combination of the gag assay failed to detect HIV-1 genomic RNA from a great number of samples.

Example 5

Amplification and Detection of HIV-1 RNA with Defined Subtypes

In this example, 33 samples harbouring HIV-1 RNA of known envelope-based subtypes were tested. The samples originate from subtyped viruses propagated in cell cultures. Samples of cell culture supernatants from both variants of group M subtypes A through H and variants of group O were spiked to HIV-1 negative human plasma and treated according to the method from example 1. Amplification and detection was performed essentially as example 4. Results are shown table 4 as the number of samples of each type from which HIV-1 RNA was detected out of the total number of each type tested.

TABLE 4

| Primer pair | HIV-1 Types | | | | | | | | | |
|---|---|---|---|---|---|---|---|---|---|---|
| | A | B | C | D | E | F | G | H | O | Total |
| SEQ ID 9/SEQ ID 5 (LTR) | 5:5 | 2:2 | 2:2 | 5:5 | 7:7 | 1:1 | 1:1 | 1:1 | 9:9 | 33:33 |
| | 4:5 | 2:2 | 2:2 | 5:5 | 6:7 | 1:1 | 1:1 | 1:1 | 0:9 | 22:33 |

HIV-1 RNA was detected from all 33 HIV-1 samples using LTR primer pair SEQ ID 9/SEQ ID 5 and probe with sequence of SEQ ID 7. In contrast, the assay using the gag primers probes combination as described in example 3 failed to detect subtype A and subtype E each from one of the samples and all samples containing HIV-1 RNA from group O members.

Example 6

Amplification and Detection of HIV-1 Clinical Samples

In this example, 7 samples obtained from seropositive patients originating from Africa, South America and Asia were assayed for the presence of HIV-1 genomic RNA. Despite the fact that blood samples from these patients are both anti-p24 antibody (Abbott Laboratories, Abbott Park, Ill.) and western blot (Genelabs) positive, all specimens were scored negative by the NASBA HIV-1 RNA QL assay (Organon Teknika BV) which uses the gag primer pair and probe combination from example 3 and only a single sample (R9612222) was detected and quantitated (29.500 RNA copies/ml) by the Quantiplex HIV-1 RNA 2.0 (Chiron) assay using a sample volume of 50 µl. In contrast, using an equal sample volume the primer pair SEQ ID 9/SEQ ID 5 and the probe with sequence of SEQ ID 7 detected four out of seven samples (Table 5).

TABLE 5

| Sample code | Country | SEQ ID 9/SEQ ID 5 (LTR) |
|---|---|---|
| R9610155 | Thailand | positive |
| R9612222 | Ghana | positive |
| R9700062 | Brazil | negative |
| R9612218 | Zaire | negative |
| R9611710 | Liberia | positive |
| R9610718 | Antilles | positive |
| R9607884 | Rwanda | negative |

The samples missed by the LTR primer probe combination are not detected due to a low viral load below the detection level since by using a sample volume of one ml the Quantiplex HIV-1 RNA 2.0 (Chiron) assay quantitated HIV-1 RNA levels of 30 or below 30 HIV-1 RNA copies per 50 µl of these samples.

The invention claimed is:

1. A method for amplifying HIV-1 nucleic acid in a sample, comprising:
   a) contacting the sample with a pair of oligonucleotide primers that bind to a first primer binding site and a second primer binding site located within the LTR region of the HIV-1 genome; and
   b) performing a nucleic acid amplification under conditions wherein said oligonucleotide primers bind only to said first and second primer binding sites, thereby amplifying HIV-1 nucleic acid in the sample;
   wherein said pair of oligonucleotide primers consists of a first primer and a second primer,
   wherein said first primer consists essentially of a first oligonucleotide that is fully complementary to a sequence of the LTR region at the first primer binding site, said oligonucleotide being 15-26 nucleotides in length and comprising at least 15 sequential nucleotides of the nucleotide sequence of:

SEQ ID NO: 1:
   G GGC GCC ACT GCT AGA GA;

said first oligonucleotide being operably linked to a promoter; and
   wherein said second primer consists essentially of a second oligonucleotide that is fully complementary to a sequence which is the reverse complement of a sequence of the LTR region at the second primer binding site, said oligonucleotide being 10-26 nucleotides in length and comprising at least 10 sequential nucleotides of the nucleotide sequence of:

SEQ ID NO: 5:
   CTC AAT AAA GCT TGC CTT GA.

2. The method of claim 1, wherein said second oligonucleotide that is fully complementary to a sequence which is the reverse complement of a sequence of the LTR region is 15-26 nucleotides in length and comprises at least 15 sequential nucleotides of the nucleotide sequence of:

```
SEQ ID NO: 5:
CTC AAT AAA GCT TGC CTT GA.
```

3. The method of claim 1, wherein said first oligonucleotide comprises the nucleotide sequence of:

```
SEQ ID NO: 1:
G GGC GCC ACT GCT AGA GA.
```

4. The method of claim 1, wherein performing a nucleic acid amplification comprises contacting the sample with one or more probe oligonucleotides selected from:

```
SEQ ID NO: 6:
TCT GGT AAC TAG AGA TCC CTC

SEQ ID NO: 7:
TAG TGT GTG CCC GTC TGT

SEQ ID NO: 8:
AGT GTG TGC CCG TCT GTT
``` one or more of which are provided with a detectable label, under conditions where hybridization can occur; and
   detecting the presence of the label in any hybrids formed between the amplified sequence and the one or more probe oligonucleotides.

5. The method of claim 1, wherein said promoter is a T3, T7, or SP6 promoter.

6. A method for amplifying HIV-1 nucleic acid in a sample, comprising:
   a) contacting the sample with a primer set that bind to a first primer binding site and a second primer binding site located within the LTR region of the HIV-1 genome; and
   b) performing a nucleic acid amplification under conditions wherein said oligonucleotide primers bind only to said first and second primer binding, thereby amplifying HIV-1 nucleic acid in the sample;
   wherein said primer set consists of a first primer and a second primer,
   wherein said first primer consists essentially of a first hybridizing oligonucleotide that is fully complementary to a sequence of the LTR region at the first primer binding site, said oligonucleotide being 15-26 nucleotides in length and comprising at least 15 sequential nucleotides of the nucleotide sequence of:

```
SEQ ID NO: 1:
G GGC GCC ACT GCT AGA GA;
``` said first hybridizing oligonucleotide being operably linked to a promoter; and
   wherein said second primer consists essentially of a second hybridizing oligonucleotide that is fully complementary to a sequence which is the reverse complement of a sequence of the LTR region at the second primer binding site, said oligonucleotide being 10-26 nucleotides in length and comprising at least 10 sequential nucleotides of the nucleotide sequence of:

```
SEQ ID NO: 5:
CTC AAT AAA GCT TGC CTT GA.
```

7. The method of claim 6, wherein said second oligonucleotide that is fully complementary to a sequence which is the reverse complement of a sequence of the LTR region is 15-26 nucleotides in length and comprises at least 15 sequential nucleotides of the nucleotide sequence of:

```
SEQ ID NO: 5:
CTC AAT AAA GCT TGC CTT GA.
```

8. The method of claim 6, wherein said first oligonucleotide comprises the nucleotide sequence of:

```
SEQ ID NO: 1:
G GGC GCC ACT GCT AGA GA.
```

9. The method of claim 6, wherein performing a nucleic acid amplification comprises contacting the sample with one or more probe oligonucleotides selected from:

```
SEQ ID NO: 6:
TCT GGT AAC TAG AGA TCC CTC

SEQ ID NO: 7:
TAG TGT GTG CCC GTC TGT

SEQ ID NO: 8:
AGT GTG TGC CCG TCT GTT
``` one or more of which are provided with a detectable label, under conditions where hybridization can occur; and
   detecting the presence of the label in any hybrids formed between the amplified sequence and the one or more probe oligonucleotides.

10. The method of claim 6, wherein said promoter is a T3, T7, or SP6 promoter.

11. A method for amplifying HIV-1 nucleic acid in a sample, comprising:
   a) contacting the sample with a pair of oligonucleotide primers that bind to a first primer binding site and a second primer binding site located within the LTR region of the HIV-1 genome; and
   b) performing a nucleic acid amplification under conditions wherein said oligonucleotide primers bind only to said first and second primer binding sites, thereby amplifying HIV-1 nucleic acid in the sample;
   wherein said pair of oligonucleotide primers consists of a first primer and a second primer,
   wherein said first primer consists essentially of a first hybridizing oligonucleotide that is fully complementary to a sequence of the LTR region at the first primer binding site, said oligonucleotide being 15-26 nucleotides in length, wherein said first hybridizing oligonucleotide comprises at least 15 sequential nucleotides of the nucleotide sequence of:

```
SEQ ID NO: 1:
G GGC GCC ACT GCT AGA GA;
``` said hybridizing oligonucleotide being operably linked to a promoter; and
   wherein said second primer consists essentially of a second hybridizing oligonucleotide that is fully complementary to a sequence which is the reverse complement of a sequence of the LTR region at the second primer binding site, said oligonucleotide being 10-26 nucleotides in length, wherein said second hybridizing oligonucleotide comprises at least 10sequential nucleotides of the nucleotide sequence of:

SEQ ID NO: 5:
CTC AAT AAA GCT TGC CTT GA.

12. The method of claim 11, wherein said second oligonucleotide that is fully complementary to a sequence which is the reverse complement of a sequence of the LTR region is 15-26 nucleotides in length and comprises at least 15 sequential nucleotides of the nucleotide sequence of:

SEQ ID NO: 5:
CTC AAT AAA GCT TGC CTT GA.

13. The method of claim 11, wherein said first oligonucleotide comprises the nucleotide sequence of:

SEQ ID NO: 1:
G GGC GCC ACT GCT AGA GA.

14. The method of claim 11, wherein performing a nucleic acid amplification comprises contacting the sample with one or more probe oligonucleotides selected from:

SEQ ID NO: 6:
TCT GGT AAC TAG AGA TCC CTC

SEQ ID NO: 7:
TAG TGT GTG CCC GTC TGT

SEQ ID NO: 8:
AGT GTG TGC CCG TCT GTT one or more of which are provided with a detectable label, under conditions where hybridization can occur; and
    detecting the presence of the label in any hybrids formed between the amplified sequence and the one or more probe oligonucleotides.

15. The method of claim 11, wherein said promoter is a T3, T7, or SP6 promoter.

\* \* \* \* \*

UNITED STATES PATENT AND TRADEMARK OFFICE
CERTIFICATE OF CORRECTION

PATENT NO. : 9,074,262 B2
APPLICATION NO. : 14/226965
DATED : July 7, 2015
INVENTOR(S) : Goudsmit et al.

Page 1 of 2

It is certified that error appears in the above-identified patent and that said Letters Patent is hereby corrected as shown below:

In the Specification:

Column 1, Line 23: Please correct "recant" to read -- recent --
Column 2, Line 7: Please correct "being Identified." to read -- being identified. --
Column 2, Line 14: Please correct "pot gene" to read -- pol gene --
Column 2, Line 20: Please correct "any domain" to read -- env domain --
Column 2, Line 29: Please correct "gag, any and" to read -- gag, env and --
Column 3, Line 6: Please correct "Infected" to read -- infected --
Column 3, Line 52: Please correct "An Isothermal" to read -- An isothermal --
Column 4, Line 1: Please correct "olgo's are" to read -- oligo's are --
Column 4, Line 2: Please correct "to Inhibit" to read -- to inhibit --
Column 4, Line 10: Please correct "Using PCR," to read -- using PCR, --
Column 4, Line 46: Please correct "backbone Instead" to read -- backbone instead --
Column 6, Line 19: Please correct "Invention" to read -- invention --
Column 6, Line 30: Please correct "Just" to read -- just --
Column 6, Line 34: Please correct "Just" to read -- just --
Column 7, Line 53: Please correct "Invention" to read -- invention --
Column 8, Line 14: Please correct "Olgonucle-" to read -- Oligonucle- --
Column 8, Line 30: Please correct "art Said" to read -- art. Said --
Column 8, Line 33: Please correct "blotin, or" to read -- biotin, or --
Column 8, Line 61: Please correct "EP95/01288." to read -- EP95/01268. --
Column 9, Line 4: Please correct "Internal" to read -- internal --
Column 9, Line 9: Please correct "EP 93/102248." to read -- EP 93/02248. --
Column 9, Line 14: Please correct "Isolation" to read -- isolation --
Column 9, Line 39: Please correct "EP0389083." to read -- EP0389063. --
Column 9, Line 42: Please correct "9001 of" to read -- 900 µl of --
Column 10, Line 2: Please correct "Isolated" to read -- isolated --
Column 10, Line 3: Please correct "Incubated" to read -- incubated --
Column 10, Line 24: Please correct "myloablastosis" to read -- myeloblastosis --

Signed and Sealed this
Seventh Day of June, 2016

Michelle K. Lee
*Director of the United States Patent and Trademark Office*

CERTIFICATE OF CORRECTION (continued)
U.S. Pat. No. 9,074,262 B2

Column 10, Line 41: Please correct "sodumnitrate," to read -- sodiumcitrate, --
Column 10, Line 41: Please correct "NatHPO$_4$NaH$_2$PO$_4$" to read -- Na$_2$HPO$_4$/NaH$_2$PO$_4$ --
Column 10, Line 42: Please correct "Incubating" to read -- incubating --
Column 10, Line 46: Please correct "mM NaeHPO$_4$" to read -- mM Na$_2$HPO$_4$ --
Column 10, Lines 59 and 60: Please correct "methyllsothiazolone"
                              to read -- methylisothiazolone --
Column 10, Line 62: Please correct "blotin" to read -- biotin --
Column 10, Line 65: Please correct "(Tris(2,2-bipyridine)" to read -- (Tris[2.2-bipyridine] --
Column 10, Line 67: Please correct "sodumcirate," to read -- sodiumcitrate, --
Column 11, Line 22: Please correct "extent Analytical" to read -- extent. Analytical --

In the Claims:

Column 19, Claim 6, Line 40: Please correct "binding, thereby" to read -- binding sites, thereby --
Column 20, Claim 11, Line 66: Please correct "10sequential" to read -- 10 sequential --

```
SEQUENCE LISTING

<160> NUMBER OF SEQ ID NOS: 14

<210> SEQ ID NO 1
<211> LENGTH: 18
<212> TYPE: DNA
<213> ORGANISM: Artificial
<220> FEATURE:
<223> OTHER INFORMATION: Oligonucleotide primer sequence

<400> SEQUENCE: 1
gggcgccact gctagaga                                                    18

<210> SEQ ID NO 2
<211> LENGTH: 20
<212> TYPE: DNA
<213> ORGANISM: Artificial
<220> FEATURE:
<223> OTHER INFORMATION: Oligonucleotide primer sequence

<400> SEQUENCE: 2
gttcgggcgc cactgctaga                                                  20

<210> SEQ ID NO 3
<211> LENGTH: 15
<212> TYPE: DNA
<213> ORGANISM: Artificial
<220> FEATURE:
<223> OTHER INFORMATION: Oligonucleotide primer sequence

<400> SEQUENCE: 3
cgggcgccac tgcta                                                       15

<210> SEQ ID NO 4
```

```
<211> LENGTH: 20
<212> TYPE: DNA
<213> ORGANISM: Artificial
<220> FEATURE:
<223> OTHER INFORMATION: Oligonucleotide primer sequence

<400> SEQUENCE: 4
ctgcttaaag cctcaataaa                                              20

<210> SEQ ID NO 5
<211> LENGTH: 20
<212> TYPE: DNA
<213> ORGANISM: Artificial
<220> FEATURE:
<223> OTHER INFORMATION: Oligonucleotide primer sequence

<400> SEQUENCE: 5
ctcaataaag cttgccttga                                              20

<210> SEQ ID NO 6
<211> LENGTH: 21
<212> TYPE: DNA
<213> ORGANISM: Artificial
<220> FEATURE:
<223> OTHER INFORMATION: Oligonucleotide probe sequence

<400> SEQUENCE: 6
tctggtaact agagatccct c                                            21

<210> SEQ ID NO 7
<211> LENGTH: 18
<212> TYPE: DNA
<213> ORGANISM: Artificial
<220> FEATURE:
<223> OTHER INFORMATION: Oligonucleotide probe sequence

<400> SEQUENCE: 7
tagtgtgtgc ccgtctgt                                                18

<210> SEQ ID NO 8
<211> LENGTH: 18
<212> TYPE: DNA
<213> ORGANISM: Artificial
<220> FEATURE:
<223> OTHER INFORMATION: Oligonucleotide probe sequence

<400> SEQUENCE: 8
agtgtgtgcc cgtctgtt                                                18

<210> SEQ ID NO 9
<211> LENGTH: 47
<212> TYPE: DNA
<213> ORGANISM: Artificial
<220> FEATURE:
<223> OTHER INFORMATION: Oligonucleotide primer sequence

<400> SEQUENCE: 9
aattctaata cgactcacta tagggagagg ggcgccactg ctagaga                47

<210> SEQ ID NO 10
<211> LENGTH: 49
<212> TYPE: DNA
<213> ORGANISM: Artificial
```

```
<220> FEATURE:
<223> OTHER INFORMATION: Oligonucleotide primer sequence

<400> SEQUENCE: 10
aattctaata cgactcacta tagggagagg ttcgggcgcc actgctaga            49

<210> SEQ ID NO 11
<211> LENGTH: 40
<212> TYPE: DNA
<213> ORGANISM: Artificial
<220> FEATURE:
<223> OTHER INFORMATION: Oligonucleotide primer sequence

<400> SEQUENCE: 11
aattctaata cgactcacta tagggcgggc gccactgcta                      40

<210> SEQ ID NO 12
<211> LENGTH: 30
<212> TYPE: DNA
<213> ORGANISM: Artificial
<220> FEATURE:
<223> OTHER INFORMATION: Oligonucleotide primer sequence

<400> SEQUENCE: 12
gatgcatgct caataaagct tgccttgagt                                 30

<210> SEQ ID NO 13
<211> LENGTH: 25
<212> TYPE: DNA
<213> ORGANISM: Artificial
<220> FEATURE:
<223> OTHER INFORMATION: Biotinylated oligonucleotide probe sequence

<400> SEQUENCE: 13
tgttaaaaga gaccatcaat gagga                                      25

<210> SEQ ID NO 14
<211> LENGTH: 24
<212> TYPE: DNA
<213> ORGANISM: Artificial
<220> FEATURE:
<223> OTHER INFORMATION: ECL labeled oligonculeotide probe sequence

<400> SEQUENCE: 14
gaatgggata gagtgcatcc agtg                                       24
```